United States Patent [19]

Lange et al.

[11] 4,069,336

[45] Jan. 17, 1978

[54] (2-OXO-PYRROLIDINES)-ACETIC HYDRAZIDES

[75] Inventors: Fritz-Walter Lange, Gauting; Haireddin Jacobi, Leichlingen, Rhineland; Jens Müller, Gauting, all of Germany

[73] Assignee: Chemisches Laboratorium Fritz-Walter Lange GmbH & Co KG, Gauting, Germany

[21] Appl. No.: 661,138

[22] Filed: Feb. 25, 1976

[51] Int. Cl.$^2$ .................... A61K 31/40; C07D 207/26; C07D 403/12
[52] U.S. Cl. ................................ 424/274; 260/326.25; 260/326.43
[58] Field of Search ...................... 260/326.43, 326.25; 424/274

[56] References Cited

U.S. PATENT DOCUMENTS

| 2,993,021 | 7/1961 | Bavley et al. | 260/326.25 |
| 3,459,738 | 8/1969 | Morren et al. | 260/326.25 |

FOREIGN PATENT DOCUMENTS

| 2,507,576 | 9/1975 | Germany | 260/326.43 |

Primary Examiner—Richard J. Gallagher
Assistant Examiner—Mary C. Vaughn
Attorney, Agent, or Firm—DeLio and Montgomery

[57] ABSTRACT

The present invention pertains to novel (2-oxo-pyrrolidine-1)-acetic hydrazides, methods for preparation and subsequent treatment therewith, and pharmaceutical preparations containing the same.

5 Claims, 2 Drawing Figures

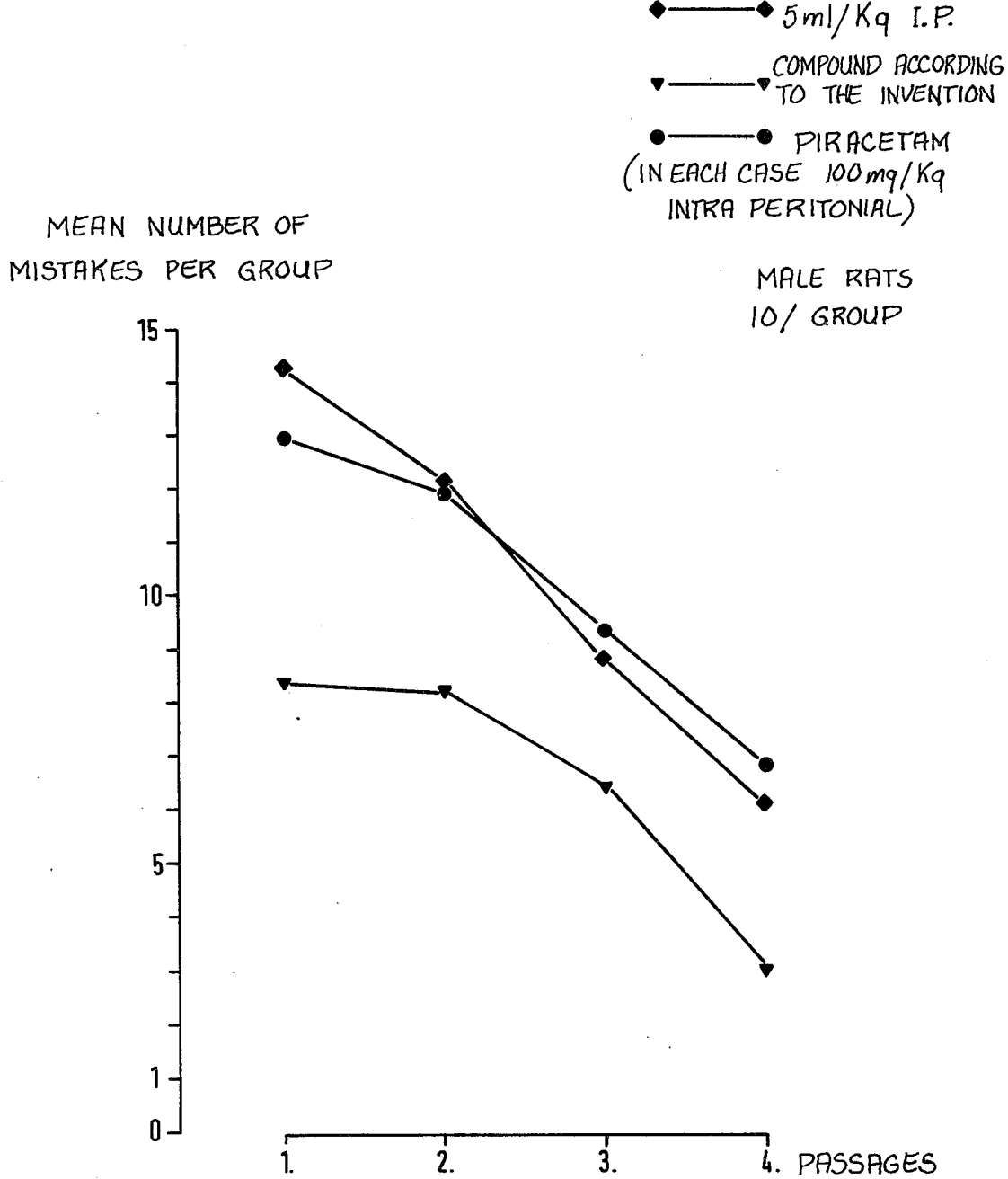

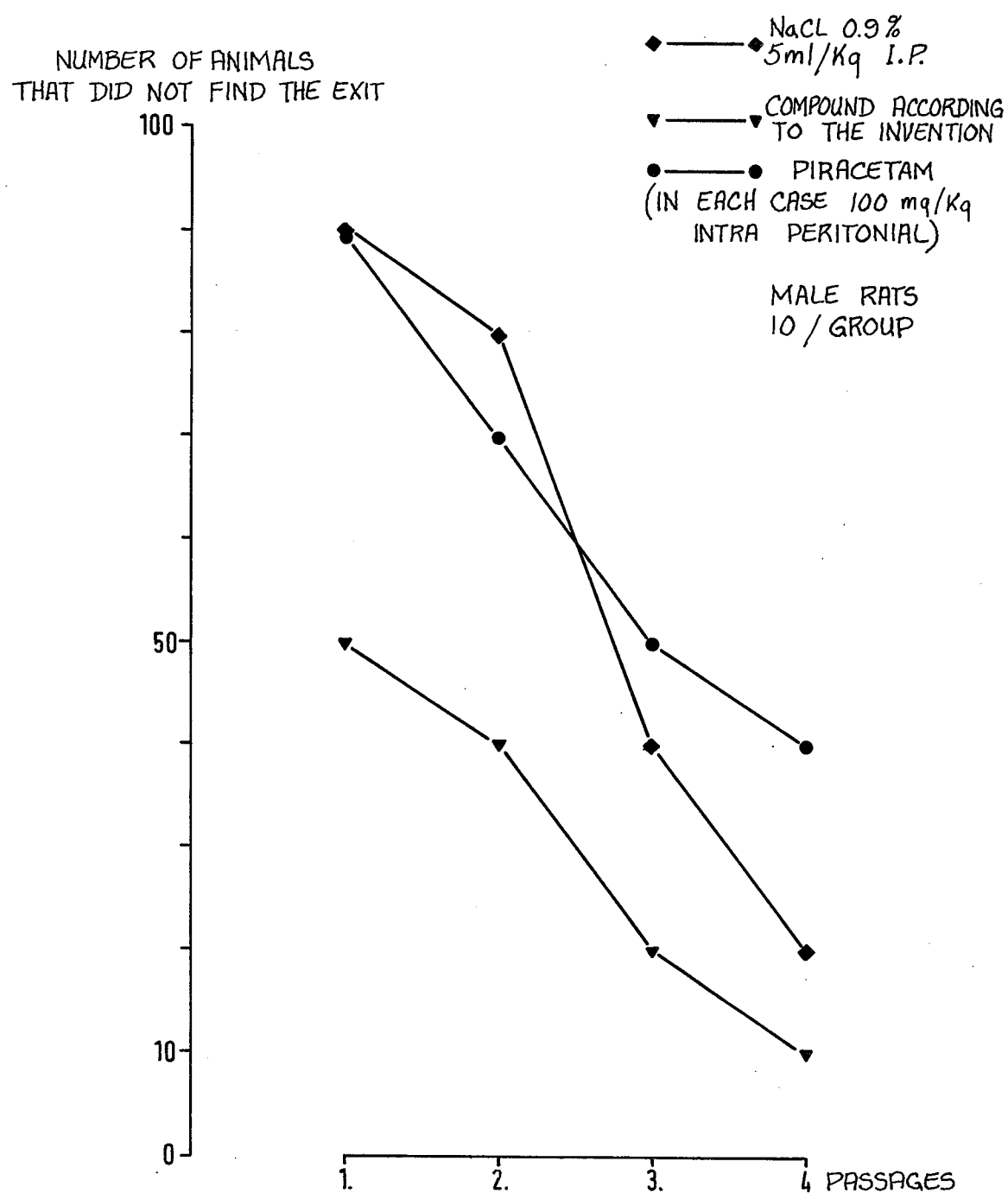

(2-OXO-PYRROLIDINES)-ACETIC HYDRAZIDES

The invention concerns novel (2-oxo-pyrrolidine-1)-acetic hydrazides. These hydrazides and 1,2-bishydrazides, respectively, offer special advantages as starting substances in the preparation of piracetam. These hydrazides also have as such a superior pharmacological effect e.g. as psychopharmacons (nootropic substances).

The substance (2-oxo-pyrrolidine-1)-acetamide has been used recently under the generic name piracetam as a drug against traveling sickness, for the treatment of senile involution (A. J. Stepink, Arzmeimittelforschung 22, 1972, No. 6, p. 975/977) and as a nootropic agent for influencing the learning capacity. (W. Strehl, A. Brosswitz, Therapiewoche 36, 1972, p. 2975). According to J. Charbaut et al (Ann. Med. Psychol. 1, 1973, p. 281/286) an improvement was found only in 45% of geriatric patients, while 40% showed no improvement.

From German Offenlegungsschrift No. 1,620,608 it is known to prepare (2-oxo-pyrrolidine-1) acetamide from (2-oxo-pyrrolidine-1) acetic ethyl ester by amidation with ammonia. But the products obtained according to this process are very impure and must be recrystallized repeatedly for purification. This requires not only a considerable technical effort, but also leads to yield losses. Besides, an extreme excess of ammonia is required in this process, namely 10 times more $NH_3$ than is stoichiometrically required for the reaction. Thus, more than 9 moles of ammonia must be removed per mole (2-oxo-pyrrolidine-1) acetamide and be processed at great costs and/or be removed. Besides, this known process requires considerable amounts of solvent. This complicates the process further and increases the costs. Other disadvantages are present in the known process, e.g. in handling the apparatus and in view of environment protection, resulting from the fact that ammonia is constantly introduced in gaseous form during the reaction.

One object of the invention is to provide compounds and methods for their preparation which have a superior effectiveness as psychopharmacons. Another object of the invention is to make chemical compounds available which permit simplification of the reaction and in the handling of the apparatus during the reaction to the corresponding acetamides, which avoid at the same time the use of great excesses of reaction components.

These objectives are achieved according to the invention by means of the new (2-oxo-pyrrolidine-1) acetic hydrazides of the formula

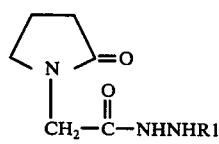

I where R1 denotes a hydrogen atom or a group of the formula

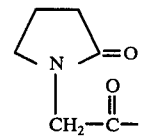

II

These new hydrazides are obtained by reacting (2-oxo-pyrrolidine-1) acetic esters of the formula

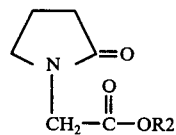

III where R2 denotes an alkyl group with 1 to 4 C-atoms, with hydrazine or with a hydrazine derivative of formula I, where R1 denotes a hydrogen atom.

In a special embodiment, it is provided in this process that (2-oxo-pyrrolidine-1) acetic ester of formula III is used, where R2 denotes —$CH_3$ or —$C_2H_5$.

A special advantage of this process is that the (2-oxo-pyrrolidine-1) acetic ethyl ester used as a starting substance, for example, can be employed in a technical quality or in crude form, as it is obtained from its method of production. If we want to use presently known (2-oxo-pyrrolidine-1) acetic esters, we find that these are available only in a very impure form and are difficult and expensive to purify because of their high boiling points. The impurity of these acetic esters is of no importance in the process according to the invention, because the hydrazide is always formed in a smooth reaction and the hydrazides obtained are very pure.

The reaction of the (2-oxo-pyrrolidine-1) acetic esters of formula III with hydrazine is generally exothermic and therefore begins spontaneously when the components are mixed with each other. The reaction rate depends, among other things, upon the reactivity of the ester groupings. The temperature of the mixture, which already begins to react at room temperature, for example, can be increased either by developing its own heat of reaction or by supplying external heat. This way the reaction rate is adapted to the reactivity of the components.

The use of (2-oxo-pyrrolidine-1) acetic methyl ester is preferred, because of the reactivity of the ester. But we could also just as well use the ethyl ester, propyl ester, isopropyl ester or the butyl esters.

It is advisable to use additionally for this reaction low alkanols, such as methanol or isopropanol. The use of a solvent permits one to control the reaction more accurately and to regulate the temperature increase up to a certain amount. The additional use of a solvent also affects the heat distribution in the reaction mixture, the reaction rate, and, therefore, also the total reaction time. If the temperature of the mixture is increased, after mixing the components (by adding into the ester), up to the boiling point of the solvent, this temperature can also be regulated accurately by the selected solvent. Thus, for example, in the reaction with acetic methyl ester in methanol or isopropanol, the heating is continued for several hours with reflux after the components have been mixed. Subsequently, the desired hydrazide is crystallized from the cold reaction mixture and can be easily isolated, washed with a solvent, and dried at room temperature.

Substantially molar ratios are required for the reaction of the ester of formula III with hydrazine for the formation of the hydrazides, e.g. 1 mole ester per 1 mole hydrazine. Preferably, however, a slight excess of hydrazine is used, e.g., 1.1 or 1.2 mole hydrazine per 1 mole ester. In this process the ordinary available technical grade hydrazine hydrate can be used. If solvents are used which contain small amounts of water, and/or hydrazine hydrate, the water is first separated by acetropic distillation, so that it does not interfere with the reaction.

If less than 1 mole hydrazine is used per mole ester, for example, 0.9 mole hydrazine, this does not result in any disadvantages, despite the theoretical excess of ester in the reaction mixture. With excess ester, the originally formed hydrazine of formula I, where R1 denotes a hydrogen atom, can further react with the ester, forming the hydrazide of formula I, wherein R1 denotes a group of formula II. When both hydrazines are formed this way, side by side, it is not difficult to separate these two substances from each other.

The hydrazide of formula I, where R1 denotes hydrogen, is soluble, for example, in hot methanol or hot isopropanol, but the hydrazide of formula I where R1 denotes a group of formula II is only soluble in hot methanol. This means that one compound can be separated first with hot isopropanol.

The hydrazide of formula I where R1 denotes a group of formula II, namely 1,2-bis-(2-oxo-pyrrolidine-1) acetic hydrazide, is generally formed at elevated temperature (above 50° C, and preferably between 100° and 180° C), with only small amounts of solvent, or without any solvent, and with a corresponding excess of ester, if we start from hydrazine as the second reaction component, or by direct reaction between the (2-oxo-pyrrolidine-1) acetic hydrazide and the (2-oxo-pyrrolidine-1) acetic ester. If solvents with a higher boiling point are used and in smaller amounts, for example, such as butanols or isopropanol or mixtures thereof, the formation of 1,2-bis-hydrazide can be increased with the corresponding quantitative ratios of the starting substances. The use of small amounts of solvent has the advantage that a crystal sludge is obtained which is suspended in the solvent and which can be easily processed. Besides, (2-oxo-pyrrolidine-1) acetic hydrazide and (2-oxo-pyrrolidine-1) acetic methyl ester can be mixed as starting components without a solvent, heated and the pure 1,2-bis-hydrazide can be obtained by redissolution in methanol.

(2-oxo-pyrrolidine-1) acetic methyl ester is obtained by reacting a (2-oxo-pyrrolidine-1) metal compound of the formula

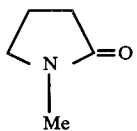

IV where Me denotes an alkaline metal atom, with monohalogen acetic ester, using a monohalogen acetic methyl ester as a monohalogen acetic ester.

Preferably monochlorine and/or monobromine acetic methyl ester is used. Preferred metal compounds of the above formula IV are (2-oxo-pyrrolidine-1) lithium, (2-oxo-pyrrolidine-1) sodium or (2-oxo-pyrrolidine-1) potassium. The reaction is preferably carried out in a non-polar or slightly polar organic solvent or in mixtures thereof. Preferred solvents are e.g. benzene, toluene and/or hexane.

The (2-oxo-pyrrolidine-1) acetic methyl ester thus obtained is much more suitable for further reaction on the ester grouping. This methyl ester has a boiling point which is lower by 12° C than the corresponding ethyl ester; consequently it can be purified much more easily and very gently by distillation. This is of particular importance since the pyrrolidine ring can be split by higher thermal stress, so that deep black resinous impurities are formed. Furthermore, the use of the acetic methyl ester results in a better space-time yield in consequent reactions. The acetamide obtained over the corresponding hydrazide or a hydrazide derivative is much purer than that obtained by starting from (2-oxo-pyrrolidine-1) acetic ethyl ester.

The (2-oxo-pyrrolidine-1) metal compound of formula IV is obtained from pyrrolidine of the formula

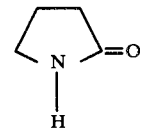

in an organic solvent with an alkali amide, for example, sodium amide, or with an alkaline metal alkyl, such as butyl-lithium. Instead of sodium amide or butyl lithium the analogous derivatives of the other alkaline metals or other alkyls can also be used. The (2-oxo-pyrrolidine-1) metal compounds are produced in the known manner. The metal compounds thus obtained need not be isolated from the corresponding solution of the (2-oxo-pyrrolidine-1) metal compounds. Rather, these solutions can be used directly for further reaction with the monohalogen-acetic methyl ester, which is a special advantage of the process of the invention, since it permits one to work continuously in the same apparatus. Thus, no yields are lost in the isolation of intermediate products. Of particular advantage also are the low equipment costs.

The (2-oxo-pyrrolidine-1) acetic hydrazides of formula I can be transformed by reduction or hydration into (2-oxo-pyrrolidine-1) acetamide of extremely pure form. For this reaction the hydrazides of formula I can be used, both in the form of where R1 denotes hydrogen, and in the other form where R1 denotes a group of formula II. Mixtures of these two substances can also be used without any disadvantage. Consequently the hydrazides according to the invention, which can be easily isolated in a very pure form, or need not be isolated if they are obtained from a process variant (solvent, temperature, molar ratios etc.) in a mixture.

With the process according to the invention the the hydrazides are obtained in a substantially quantitative yield:

Pharmacological effectiveness

The compounds according to the invention showed a greater nootropic activity in animal tests than piracetam according to the state of the art, and thus they represent an enrichment of the pharmacological field.

For a pharmacological comparison between the compound 1,2-bis-(2-oxo-pyrrolidine-1) acetic hydrazine according to the invention with piracetam we used male rats of 150–200 g weight, which were divided by means of a random table into three groups of 10 animals each. After we had made sure in a preliminary test that the animals could not find their way to the exit of a water labyrinth within 5 minutes (method based on C. Giurgea et al, Pharmacol. (Paris) 3, 1972, p. 17–30), the groups were exposed before the test proper on four successive days and on the 7th day to a deficit of oxygen, in order to cause brain damage. This was done by introducing nitrogen into a desiccator after displacing the air. The animals remained in the vessel for a sufficient length of time until they assumed a lateral position under anoxemic cramps. 30 minutes before they were introduced into the nitrogen atmosphere each animal of a group was given introperitoneally (i.p.) 100 mg 1,2-bis-(2-oxo-pyrrolidine-1) acetic hydrazide, or 100 mg piracetam or, in the control group, a corresponding volume of a physiological salt solution per kg body weight. On the days when the passage through the water labyrinth was tested, the animals were put into the labyrinth after the nitrogen atmosphere had been removed, and the mistakes which the animals made until they reached the exit and the number of animals which did not find the exit at all within the test period were recorded.

The tests were carried out according to the method of the simple blind tests, that is, the laboratory technician who supervised the tests was not informed as to which animals belonged to which group.

It can be seen from the curves in FIG. 1, the piracetam did not influence the frequency of mistakes in the test animals, that is, control animals and piracetam animals made the same number of mistakes, but those treated with the compound according to the invention made far fewer mistakes. In the evaluation of the curves according to the test, a statistical security with an error probability of less than 5% was found in individual points of the curves.

In FIG. 2 the percentage of animals which had not found the exit of the labyrinth in a given time unit is plotted on the ordinate. In this type of evaluation it could also be shown that piracetam did not influence the behavior of the animals, while more animals of the group treated with the compound according to the invention had reached the exit of the labyrinth.

It should be emphasized that these results were obtained with equal doses of the compound according to the invention and of piracetam, namely 100 mg per kg body weight. Since the molar weights of 1-bis-(2-oxo-pyrrolidine-1) acetic hydrazine and piracetam are in a ratio of 1:2, it could be shown by these tests that the compound according to the invention is twice as effective as piracetam.

In order to further prove the pharmacological superiority of the compound according to the invention over piracetam, rabbits were initially given (2-oxo-pyrrolidine-1) acetic hydrazide and, 1 hour later, given the sodium salt of 5-ethyl-3-(1-methylbutyl)-barbituric acid to produce artificial intoxication.

Piracetam and (2-oxo-pyrrolidine-1) acetic hydrazide were administered in a dose of 100 mg/kg, one hour before 5-ethyl-5-(1-methylbutyl)-barbituric acid (phenolbarbital-sodium 40 mg/kg i.v.) was given and the following results were obtained:

| lethality: | control (NaCl i.v.) | 3/7 = 43% |
|---|---|---|
| | piracetam | 2/5 = 40% |
| | (2-oxo-pyrrolidine-1) acetic hydrazide | 0/5 = 0% |

It was thus found that the compound according to the invention completely prevented death.

The present invention also comprises pharmaceutical preparations which contain, in addition to non-toxic, inert pharmaceutical carrier substances, the active substance according to the invention, as well as methods for the preparation of these compounds.

The present invention also comprises pharmaceutical preparations in dosage units. This means that the preparations are available in the form of individual parts, e.g. tablets, dragees, capsules, pills, whose active substance is a fraction or a multiple of a single dose. The dosing units can contain, for example, 1, 2, 3 or 4 single doses or ½, ⅓ or ¼ of a single dose. A single dose contains preferably the amount of active substance which is administered in one application and which corresponds usually to a whole, a half, a third or quarter of a single dose.

By non-toxic, inert pharmaceutically suitable carrier substances we mean solid, semi-solid, or liquid diluents, fillers or formulation aids of any type.

Preferred pharmaceutical preparations are tablets, dragees, capsules, pills, pellets, solutions, suspensions and emulsions, as well as powders.

Tablets, dragees, capsules, pills and pellets can contain the active substance, in addition to the common carrier substances, like fillers and diluents, binders, moisturizers, explosives, solution inhibitors, resorption accelerators, wetting agents, adsorbents, lubricants or mixtures of these substances.

The tablets, dragees, capsules, pills and pellets can be provided with the usual coatings and coverings containing opaquing agents, if necessary.

The active substance can also be contained in microcapsules with one or more of the above indicated carrier substances.

The therapeutically effective compounds should be contained in the above-mentioned pharmaceutical preparations preferably in a concentration of about 0.1 to 99.5%, and preferably 0.5 to 95%, by weight of the total mixture.

The above indicated pharmaceutical preparations can also contain additional pharmaceutically active substances, in addition to the active substance according to the invention.

The above indicated pharmaceutical preparations are produced in the known manner according to known methods, for example, by mixing the active substance(s) with the carrier substance(s).

The present invention also comprises the use of the active substance according to the invention, as well as of pharmaceutical preparations which contain the active substance according to the invention, in human and veterinary medicine to prevent, improve or cure diseases which can occur in the cerebral functional region. These are, for example, chronic brain disfunctions, such as cerebral schlerosis, weakness of memory after circulatory disorders as a result of alcoholism or traumatic experiences.

In general, it was found expedient to administer the active substance according to the invention in total amounts of about 1.2 to about 2.4 g per 24 hours, if necessary, in the form of several single doses to obtain the desired results. A single dose contains the active substance according to the invention preferably in amounts of about 100 to 500 mg, and preferably, 300 to 400 mg. But, it may be necessary to deviate from the above indicated doses, depending on the type and the body weight of the object to be treated, and on the type and severity of the disease.

The invention will now be described more fully by way of example.

EXAMPLE 1

Preparation of (2-oxo-pyrrolidine-1) acetic hydrazide

Into a solution of 38 g hydrazine in 200 ml isopropanol, 157 g of (1 mole (2-oxo-pyrrolidine-1) acetic methyl ester was added with stirring. The reaction was exothermic; so the addition rate was regulated.

By external influence and by regulating the addition rate, the temperature rises slowly to about 50° C. Then the reaction mixture was heated for another 3 hours with reflux. Subsequently, the reaction mixture was allowed to cool. From the cool reaction mixture the hydrazine crystallized in the form of colorless crystals. The crystal sludge was drained off, washed twice with cold isopropanol and dried at room temperature.

The hydrazide yield was 1429 g (91% of the theoretical); the melting point was 58° C.

The nitrogen determination had the following result:
N-calc. 26.74%
N found 26.87%

The mother liquor was used again, in unchanged form, in the next batch and the yield increased slightly to 96% of the theoretical.

EXAMPLE 2

Preparation of 1,2-bis-(2-oxo-pyrrolidine-1) acetic hydrazine

A mixture of 157 g (1 mole) of (2-oxo-pyrrolidine-1) acetic hydrazide and 157 g (1 mole) of (2-oxo-pyrrolidine-1) acetic methyl ester was heated for 24 hours under stirring to 150° to 170° C. The reaction mixture was allowed to cool off. After the reaction mixture had cooled to room temperature, it was heated under stirring with reflux in 400 ml methanol, until it completely dissolved.

After cooling the mixture crystallized in colorless crystals which were drained off, washed with isopropanol, and dried at 50° C. The desired hydrazide was obtained in a yield of 234.3 g (83% of the theoretical); the melting point was 203° C.

The nitrogen determination had the following result:
N-calc.: 19.85%
N-found: 19.84%

The mother liquor were used again in unchanged form for several batches and the yields increased to 94%.

EXAMPLE 3

Preparation of (2-oxo-pyrrolidine-1) acetamide 157 g (1 mole) of (2-oxo-pyrrolidine-1) acetic hydrazide was dissolved in 400 ml dry methanol and hydrated with 10 g Raney nickel at 20 excess atmospheres in a closed vessel at 100° to 120° C until hydrogen absorption had stopped. After opening the pressure vessel, the solution was filtered off hot from the catalyst; the catalyst could be used again for a new batch.

The filtrate was concentrated; the still hot concentrate was mixed with 400 ml isopropanol; subsequently the mixture was stirred cold and, after draining and washing with isopropanol, 140 g (2-oxo-pyrrolidine-1) acetamide (89% of the theory) was obtained in the form of colorless crystals with a melting point of 151° C.

The mother liquor was used again in unchanged form for several batches so that the yield increased to 95%.

The nitrogen determination had the following result:
N-calc.: 19.72%
Found : 19.73%

What is claimed is:

1. (2-oxo-pyrrolidine-1) acetic hydrazides of the formula I,

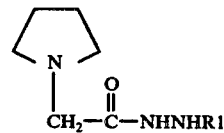

where R1 denotes a group of the formula II,

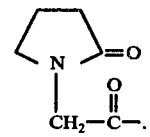

2. A pharmaceutical preparation useful as a psychopharmacon and for treatment of diseases occurring in the cerebral function region of the brain containing, as an active ingredient, an effective amount of a compound of claim 1, together with suitable pharmaceutical inert carrier and auxiliary substances.

3. The pharmaceutical preparation of claim 2, wherein said effective amount of said compound of claim 1 is between about 1.2 to 2.4 grams per 24 hours.

4. The pharmaceutical preparation of claim 2, wherein said effective amount of said compound of claim 1 is between about 100 to 500 milligrams per single dose.

5. The pharmaceutical preparation of claim 2 wherein said effective amount of said compound of claim 1 between about 300 to 400 milligrams per single dose.

* * * * *

UNITED STATES PATENT AND TRADEMARK OFFICE
CERTIFICATE OF CORRECTION

PATENT NO. : 4,069,336
DATED : January 17, 1978
INVENTOR(S) : Fritz-Walter Lange et al.

It is certified that error appears in the above-identified patent and that said Letters Patent are hereby corrected as shown below:

The title should read, as follows:  --(2-OXO-PYRROLIDINE-1)-ACETIC HYDRAZIDES--

In Column 1, line 5, the last word on that line should read --1,2-bis-hydra- --

In Column 8, lines 25-32, the chemical, structural formula:

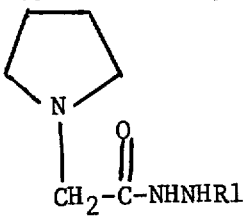

should read, as follows:

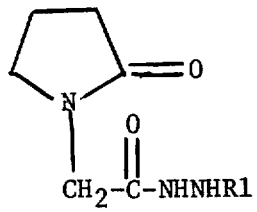

In Column 8, line 46, add --ly-- to "pharmaceutical" to read --pharmaceutically--

In Column 8, line 56, add --is-- after the phrase "of claim 1"

Signed and Sealed this

Eighteenth Day of December 1979

[SEAL]

Attest:

SIDNEY A. DIAMOND

Attesting Officer     Commissioner of Patents and Trademarks